DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 23, 1971

892 O.G. 1209

T892,001

BACTERIOSTATIC HALOARALKANOLS

Joseph W. Baker, 421 Greenleaf Drive 63122, and Ignatius Schumacher, 1009 S. Elm 63119, both of St. Louis, Mo.

Filed May 11, 1970, Ser. No. 36,382
**Int. Cl. C07c *31/14***
U.S. Cl. 260—618 D
No Drawing. 7 Pages Specification

Certain halogenated compounds represented by the formula

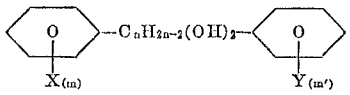

wherein $C_nH_{2n-2}$ is a saturated hydrocarbon chain;
*n* represents an integer selected from 2 through 4;
*m* and *m'* each represent an integer selected from 1, 2 or 3, provided that sum of $m+m'$ is at least equal to 4; and
X and Y represent chloro or bromo, are prepared by reduction of the corresponding diketones. The halogenated aralkanols effectively control the growth of microorganisms.